United States Patent [19]

Spani

[11] Patent Number: 4,764,166
[45] Date of Patent: Aug. 16, 1988

[54] ULTRASONIC AIR-IN-LINE DETECTOR

[75] Inventor: Wayne Spani, San Diego, Calif.

[73] Assignee: Fisher Scientific Company, Pittsburgh, Pa.

[21] Appl. No.: 86,063

[22] Filed: Aug. 17, 1987

[51] Int. Cl.$^4$ ............................................. A61M 5/14
[52] U.S. Cl. ..................................... 604/65; 604/122
[58] Field of Search ................ 73/19, 61; 604/65, 66, 604/67, 122, 123

[56] References Cited

U.S. PATENT DOCUMENTS

| | | | |
|---|---|---|---|
| 3,974,681 | 8/1976 | Namery | 73/67.5 R |
| 4,137,940 | 2/1979 | Faisandier | 604/65 |
| 4,237,878 | 12/1980 | Kobayashi et al. | 604/122 |
| 4,367,736 | 1/1983 | Gupton | 128/214 E |
| 4,418,565 | 12/1983 | St. John | 73/19 |
| 4,487,601 | 12/1984 | Lindemann | 604/122 |
| 4,496,346 | 1/1985 | Mosteller | 604/122 X |
| 4,617,014 | 10/1986 | Cannon et al. | 604/67 |
| 4,673,927 | 6/1987 | Cianciavicchia et al. | 73/19 X |

FOREIGN PATENT DOCUMENTS 181691  5/1986  European Pat. Off. .............. 604/22

Primary Examiner—Edward M. Coven
Attorney, Agent, or Firm—Workman, Nydegger & Jensen

[57] ABSTRACT

An ultrasonic device for detecting the presence of air in the fluid line of an IV infusion device comprises a transmitter and a receiver which are positioned to pinchingly engage a portion of the fluid line therebetween. Both the transmitter and receiver have convex-shaped lenses which contact and cause a slight indentation of the tube for enhanced coupling therebetween. The device may also have a pair of diametrically opposed pedestals which contact and engage the tube from a direction substantially at right angles to the axis defined by the transmitter and receiver. These pedestals help hold the tube between the transmitter and receiver. The device also includes self-testing electronic componentry which compares the transmitter-off output with the transmitter-on output to determine whether operation is normal or should be stopped because either there is air in the line or the electronic circuitry is faulty.

16 Claims, 3 Drawing Sheets

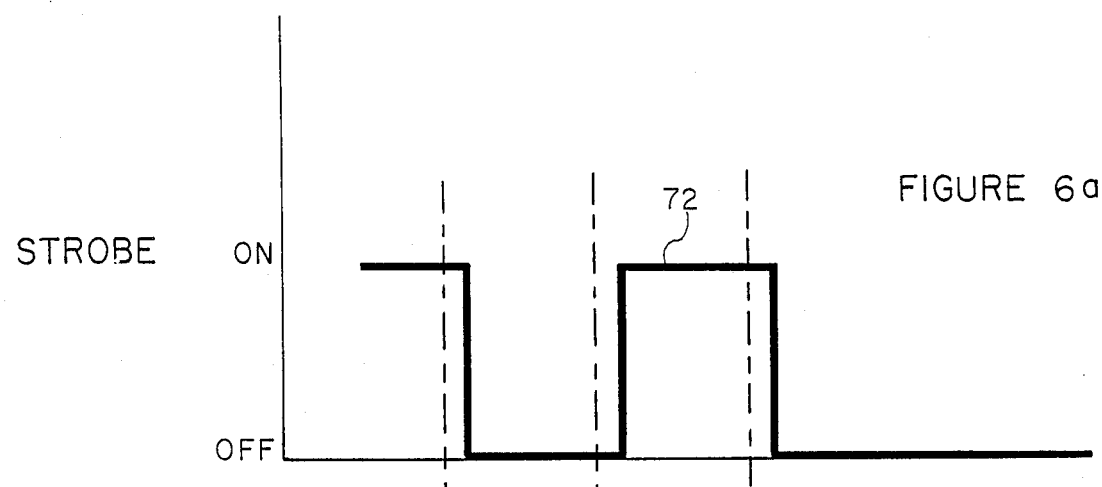
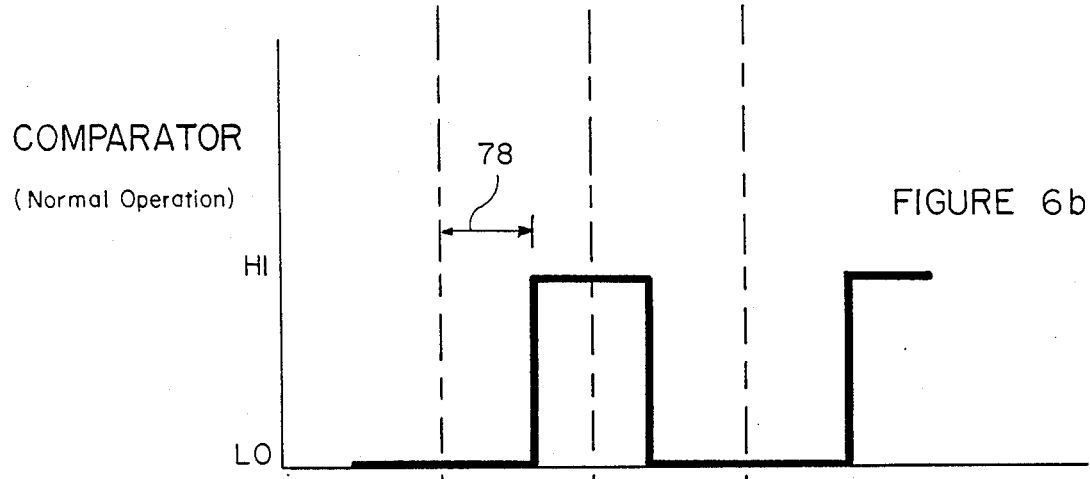
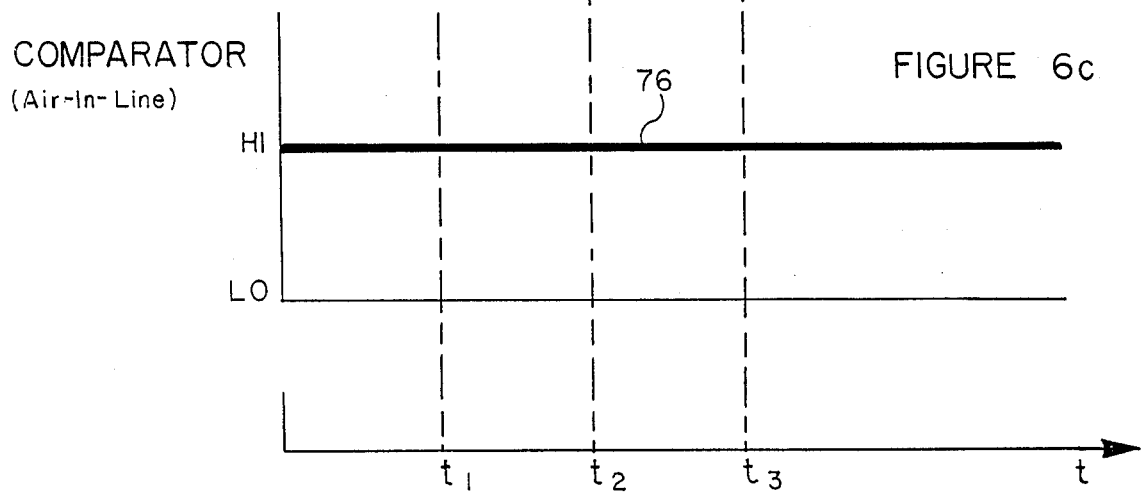

ULTRASONIC AIR-IN-LINE DETECTOR

BACKGROUND OF THE INVENTION

The present invention relates to devices useful for the detection of air embolisms in fluid lines. More particularly, the present invention relates to an untrasonic device which is engageable with a flexible tube to determine when air, rather than fluid, is flowing through the tube. The present invention is particularly, but not exclusively, useful in the health care field for detecting air-in-line conditions in an IV tube through which medical solutions are being administered.

DESCRIPTION OF THE PRIOR ART

Intravenous (IV) drug delivery systems have been used in numerous medical procedures for many years. Their efficacy is widely accepted. Always, however, whenever medical solutions are administered intravenously there is the danger that a large bolus of air may also be inadvertently administered. The potentially fatal consequences of such an accident are well known.

As might be expected, whenever a mechanical device is used in an IV administration system to assist the infusion of medical solutions to a patient, the possibility of an air leak or some other inadvertent introduction of air into the IV line is increased. Accordingly, great effort is taken in the design of IV administration systems to insure that the possibility of such an accident is made extremely unlikely. Thus, air-in-line detectors are of great importance to the safe operation of a medical infusion device.

The mere incorporation of an air-in-line detector into the system of a medical infusion device is not sufficient by itself. For any medical device to operate efficiently there must be some means for making periodic safety checks of the system. This is particularly important where air-in-line detectors are concerned. Operation of the system when there is air in the fluid line can, as previously mentioned, have catastrophic consequences. Accordingly, it is desirable that an air-in-line detector be able to periodically test itself to ensure its proper operation.

Several devices have been proposed for air-in-line detectors. Typically such devices have employed either an optical system which depends on the light transmissive characteristics of fluids or an ultrasonic system which depends on the ultrasonic energy transmissive characteristic of fluids. The present invention is concerned with ultraonsic detection of air embolisms in an IV fluid infusion tube.

A major advantage of using ultrasonic technology for the detection of air in a fluid line is the inconsequential effect of the fluid's opacity. Unlike optical systems which are greatly affected by fluid opacity, ultrasonic systems can substantially ignore this variable. On the other hand, unlike optical systems which are operative merely by properly aligning the system's elements relative to the fluid tube, an ultrasonic system, in addition to proper alignment of the elements, must also establish proper impedance matching. Essentially, this means that a direct ultrasonic energy path must be created through the fluid tube between the transmitter and receiver. Such a path requires effective contact between all aligned elements in the system. Further, in order to obtain valid indications of the air-in-line condition, alternate paths which are able to transmit ultrasonic energy between the transmitter and receiver and around the fluid tube must somehow be obstructed.

Various devices have been proposed for ultrasonic air-in-line devices which address these problems. For example, in an attempt to achieve proper impedence matching, the device disclosed in U.S. Pat. No. 4,418,565 to St. John incorporates an elastomeric material positioned between each transducer and the tube to make direct contact therebetween. U.S. Pat. No. 3,974,681 to Nanery incorporates sound pipes between the transducer and tube for this same purpose. Further, since the St. John patent discloses a single base for supporting both the transmitter and the receiver, it also discloses a slot formed therebetween to hinder the propagation of ultrasonic energy by a route other than through the elastomer members which are positioned between the receiver and the transmitter.

As an advancement from the prior disclosed devices, the present invention recognizes that enhanced impedence matching can be obtained by direct contact between the ultrasonic transducers and the fluid tube. Thus, the need for intermediate structure such as an elastomeric material or sound pipes is obviated. More particularly, the present invention recognizes that an ultrasonic transducer having a convex surface which is in direct contact with the fluid tube can be positioned to cause a slight indentation of the tube. This indentation accomplishes a dual purpose. First, it provides good coupling at the flushed interface between transducer and fluid tube which is necessary for proper operation of an ultrasonic system. Second, the indentation results from an interface fit between the tube and the transducer which holds the tube in a fixed position relative to the ultrasonic transducers.

Accordingly, it is an object of the present invention to provide an ultrasonic air-in-line detector for use with a flexible fluid tube which provides good ultrasonic coupling by positioning the ultrasonic transducers, both transmitter and receiver, into direct contact with the fluid tube. It is another object of the present invention to provide a housing for the ultrasonic transducers which will create a direct ultrasonic path through the fluid tube and hinder the propagation of ultrasonic energy by other routes. Still another object of the present invention is to provide self testing electronic circuitry which will monitor the operation of the air-in-line detector and determine when an inoperative condition exists. Yet another object of the present invention is to provide a cost effective ultrasonic air-in-line detector which is easily manufactured and easy to use.

SUMMARY OF THE INVENTION

The preferred embodiment of the ultrasonic air-in-line detector for the present invention used to detect air in a flexible fluid tube comprises a generally U-shaped base which forms a cavity between the branches of the U. An ultrasonic transmitter is mounted on one branch of the U with its associated convex lens protruding into the cavity. Likewise, an ultrasonic receiver is mounted on the opposing branch of the U with its associated convex lens protruding into the cavity. A pedestal attached at the base of the U also protrudes into the cavity. The pedestal helps stabilize the fluid tube when the tube is placed into the cavity and held between the lenses of the ultrasonic receiver and ultrasonic transmitter. With the tube so positioned in the cavity, a second pedestal can be moved into contact with the tube at a point which is subtantially diametrically opposite from the point at which the first pedestal contacts the tube. Thus, the tube is stationarily held in the cavity between the pedestals and between the convex lenses of the ultrasonic transducer. The lenses contact the tube at substantially right angles to the line on which the pedestals contact the tube.

The ultrasonic air-in-line detector of the present invention may also include electronic circuitry which is self-testing. This self-test is accomplished by periodically stopping the input to the ultrasonic transmitter and recognizing that a transmitter-off condition is substantially equivalent to an air-in-line condition. Accordingly, when the receiver cannot distinguish between a transmitter-on condition and a transmitter-off condition, either there is an air-in-line condition or the circuitry of the system is faulty.

The novel features of this invention as well as the invention itself both as to its organization and operation will be best understood from the accompanying drawings taken in conjunction with the accompanying description in which similar reference characters refer to similar parts and in which:

BRIEF DESCRIPTION OF THE DRAWINGS

FIGS. 6A, B and C are graphs of the outputs of selected electronic components of the present invention.

DESCRIPTION OF THE PREFERRED EMBODIMENT

Figure 1:
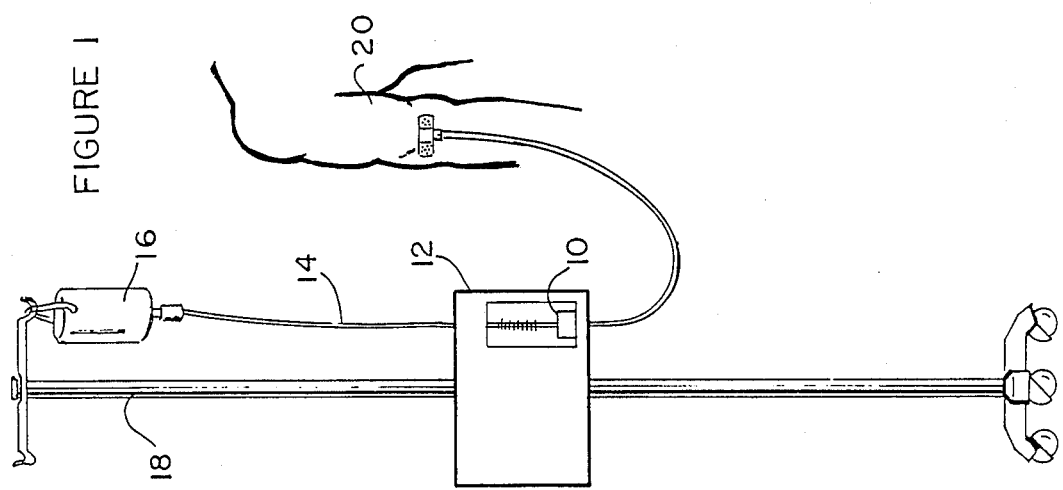
FIG. 1 is a front elevational view of the present invention in operative association with other elements of an IV infusion system.

Referring initially to FIG. 1 the air-in-line detector of the present invention, generally designated 10, is shown in operative association with an intravenous (IV) administration system. Specifically, the detector 10 is shown mounted on a medical device 12. While the detector 10 of the present invention, may be used with any IV infusion device, it is particularly well suited for operation with a device such as the one dislosed in U.S. Pat. No. 4,617,014 to Cannon et al. As shown in FIG. 1, such a device 12 is operatively connected to cooperate with an IV tube 14 for the purpose of pumping or controlling the flow of fluid through the tube 14. Typically, in medical procedures, a fluid source 16 is connected in fluid communication with tube 14 and hung from an IV pole 18. The system is then assembled for the infusion of medical solutions from source 16 to a patient 20.

Figure 2:
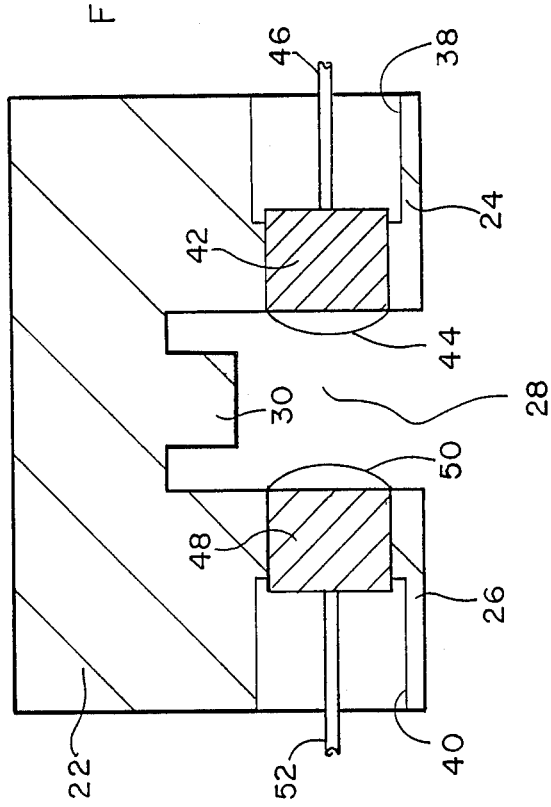
FIG. 2 is a perspective view of the detector of the present invention.

Reference to FIG. 2 shows that detector 10 has a substantially U-shaped base 22 with two oppositely extending branches 24, 26. A cavity 28 is formed between branches 24, 26 and a pedestal 30, which is attached to base 22 at the bottom of the U, protrudes into cavity 28. As will be readily appreciated by the skilled artesan, base 22 with branches 24, 26 and pedestal 30 can be of unitary construction and manufactured by processes well known in the pertinent art, such as by injection molding. FIG. 2 also shows a door 32 which is associated with base 22 by means such as the hinge 34.

It is to be understood that door 32 need not be directly hinged onto base 22. Instead, and preferably, door 32 may be hingedly attached to device 12. In either case, it is important that the pedestal 36, which is mounted on door 32, be moveable into a position wherein pedestal 36 protrudes into the cavity 28 between branches 24, 26. It will be appreciated by the skilled artesan that door 32 and pedestal 36 can be of unitary construction and manufactured by a process such as injection molding.

Figure 3:
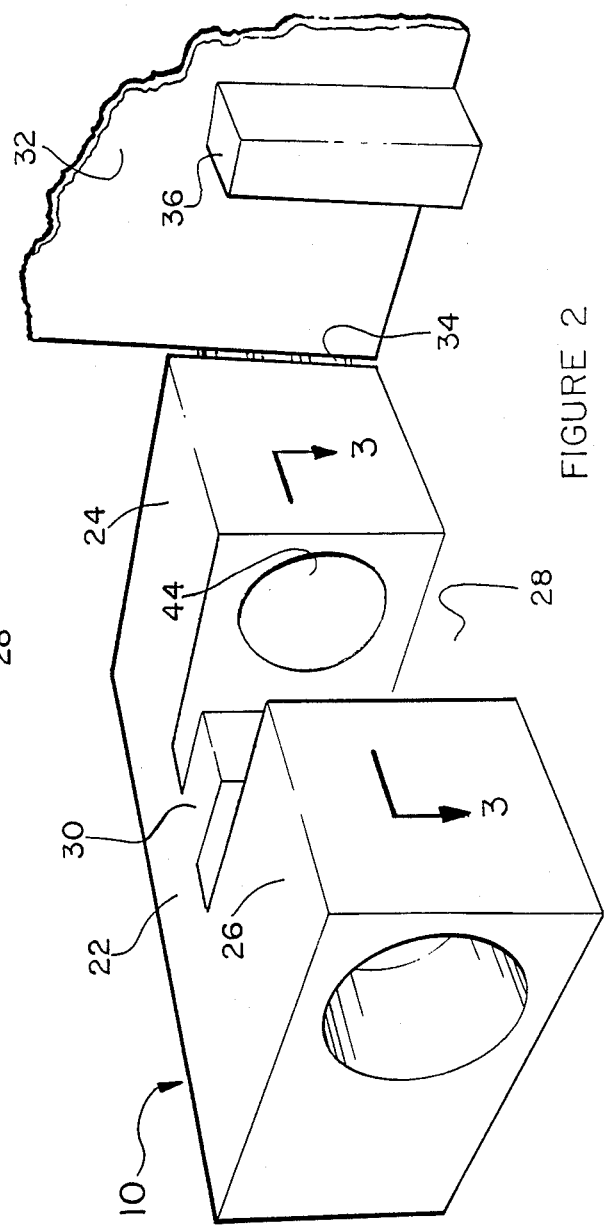
FIG. 3 is a cross-sectional view of the detector as seen along the line 3—3 in FIG. 2.

FIG. 3 is a cross-sectional view of detector 10 which shows the interaction of its components. As shown, branch 24 of detector 10 is formed with a housing 38. Likewise, branch 26 is formed with a housing 40. A piezo-electric crystal 42 is mounted in housing 38 and an acoustic lens 44, which is preferably made of an epoxy material, is attached to crystal 42 by any appropriate means, such as by an epoxy adhesive well known in the pertinent art. Also, for purposes of the present invention, crystal 42 can be made of any well known piezo ceramic material. Further, in the preferred embodiment, lens 44 is formed into a spherical convex shape with a relative curvature substantially as indicated in FIG. 3. Wiring 46 is provided to electrically connect piezo-electric crystal 42 with appropriate electronic components. For purposes of further discussion, the combination of crystal 42 and lens 44 will hereafter be sometimes generally referred to collectively as the ultrasonic transmitter.

An ultrasonic receiver is constructed in a manner similar to the construction of the transmitter and will include a piezo-electric crystal 48 which is mounted in the housing 40 of branch 26. An acoustic lens 50 is attached to crystal 48 and wiring 52 is provided to electrically connect crystal 48 with appropriate electronic componentry. Like the components of the transmitter, the receiver components are made of materials well known in the pertinent art. Specifically, crystal 48 is made of a piezo-ceramic and the spherically shaped convex lens 50 is made of an epoxy material which is attached to crystal 48 by an epoxy adhesive.

As an alternative to the epoxy material used for acoustic lenses 44 and 50, a polycarbonate material may be used. This could lead to a design in which the lenses 44 and 50 are integrally molded into the base 22. With this configuration piezo-electric crystals 42 and 48 can be respectively epoxy bonded in a manner well known in the relevant art, to lenses 44 and 50.

Figure 4:
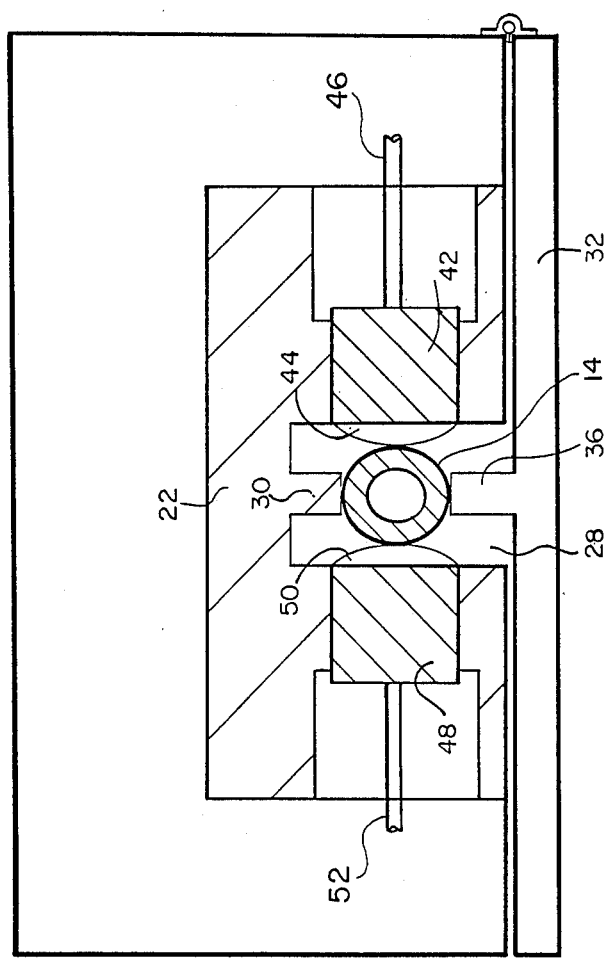
FIG. 4 is a cross-sectional view of the detector as seen in FIG. 3 with a fluid tube mounted thereon and restrained therein.

The operative placement of tube 14 into detector 10 is best seen in FIG. 4 where it can be appreciated that tube 14 is positioned in cavity 28 with lens 44 substantially diametrically opposed to lens 50. Also, tube 14 is positioned to remain in contact with pedestal 30 when door 32 is moved into position to bring pedestal 36 into contact with tube 14. As shown in FIG. 4, lens 44 can be prepositioned relative to lens 50 to pinch tube 14 therebetween when the tube 14 is placed into the cavity 28. This pinching action causes indentations of tube 14 at the respective interfaces of tube 14 with lens 44 and 50 to establish good acoustic coupling for the detector 10. Also, this cooperation of structure provides an interference fit between the tube 14 and detector 10 which will help hold tube 14 on detector 10.

The acoustical coupling of lenses 44 and 50 with tube 14 is enhanced by the action of pedestals 30 and 36 on tube 14. As seen in FIG. 4, when pedestals 30 and 36 both make contact with tube 14 they, like lenses 44 and 50, tend to pinch tube 14. This action causes a slight deformation of tube 14 which urges tube 14 into more immediate contact with lenses 44 and 50. As will be appreciated by the skilled artesan, there are competing concerns at play in this cooperation. On the one hand, there is the desire to create the maximum beneficial acoustic coupling attainable for detector 10. This requires intimate contact of lenses 44 and 50 with tube 14. On the other hand, there is the desire to minimize distortion of tube 14. This means that the pinching action of detector 10 on tube 14 must be limited to some extent. The balance of these apparently competing interests is best attained by a proper geometrical arrangement of the components of detector 10 needed to accomplish its intended operational specifications.

Figure 5:
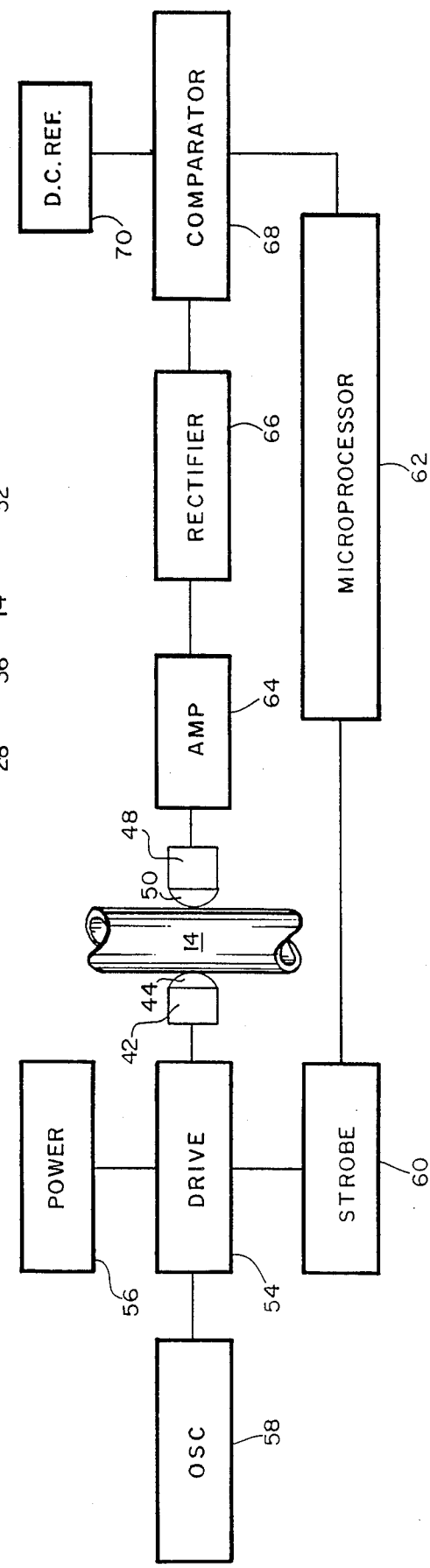
FIG. 5 is a block diagram of the electronic componentry used for the present invention.

The preferred electronic componentry necessary for activation of detector 10 is schematically shown in FIG. 5. It will be understood by the skilled artesan that all electronic components disclosed for this system are well known in the pertinent art and are commercially available. As shown in FIG. 5, tube 14 is placed in operative engagement with piezo-electric crystals 42, 48 through the mechanical coupling of lenses 44, 50 with tube 14 in a manner previously discussed. From the block diagram drawing of FIG. 5, it can be seen that piezo-electric crystal 42 serves as an ultrasonic transmitter which generates ultrasound energy according to input received from drive 54. The output from drive 54, which is input for crystal 42, is a step signal generated by the interconnection at drive 54 of power source 56 with oscillator 58 and strobe 60. Specifically, power source 56 supplies electrical power for the system while oscillator 58 causes drive 54 to generate a sinusoidal output at the resonant frequency of crystal 42. Simultaneously, strobe 60 causes drive 54 to turn ON or OFF at predetermined intervals. The result is a step input to crystal 42 that alternates between an OFF condition wherein there is no excitation of crystal 42 and an ON condition wherein crystal 42 is excited at its resonant frequency to generate ultrasound energy. Preferably, strobe 60 is operated by microprocessor 62 to cause switching between the ON and OFF condition approximately every nine milliseconds. Thus, drive 54 generates a stepped output having an eighteen millisecond cycle.

On the receiver side of detector 10, piezo-electric crystal 48 is mechanically coupled with tube 14 through lens 50 to receive signals eminating from crystal 42. In the electrical circuitry of detector 10, piezo-electric crystal 48 is electrically connected to an amplifier 64 and the output from amplifier 64 is fed directly to filter/rectifier 66. At filter/rectifier 66, this output is substantially changed from a sinusoidal signal to an amplitude modulated signal. The comparator 68 then takes the output from filter/rectifier 66 and compares it with a d.c. reference voltage from reference 70 to establish a digital output from comparator 68 which is passed to microprocessor 62.

Microprocessor 62 analyzes the digital output from comparator 68 to determine whether the device 12 is safely operating without air in tube 14. This determination is made according to an algorithm which accounts for the rate of fluid flow through tube 14 in its analysis in order to ignore very small air bubbles, i.e. bubbles of less than approximately fifty microliters, which are of no real medical concern. Also, microprocessor 62 provides input to strobe 60 to regulate its operation. With these connections, microprocessor 62 is able to analyze the output of detector 10 coming from comparator 68 in relation with the input to detector 10 beginning at strobe 60.

OPERATION

In its operation detector 10 is activated by power from source 56. IV tube 14 is operatively associated with detector 10 when it is inserted into cavity 28. This insertion brings convex-shaped acoustic lenses 44 and 50 into direct mechanical coupling with tube 14 and generates an interference fit therebetween which helps hold tube 14 in cavity 28. Door 32 is then closed onto base 22 to bring pedestal 36 into contact with tube 14. This action provides a pinching engagement of tube 14 between the diametrically opposed pedestals 30 and 36 in addition to the pinching engagement of tube 14 between the diametrically opposed lenses 44 and 50.

Operation of device 12 is intended to cause fluid flow through tube 14. Accordingly, microprocessor 62 must be capable of interpreting the output it receives from comparator 68. As is well known by the skilled artesan, the signal received by acoustic lens 50, which eventually establishes the output from comparator 68, will vary depending on whether there is fluid or air in tube 14. This, of course, results from impedance matching and the fact that fluid will transmit ultrasound energy very well whereas air will not. Thus, it is theoretically sufficient if microprocessor 62 is merely able to distinguish between the two resultant signals. Unfortunately, too many adverse possiblities exist for such a simple system to be reliable. As a consequence the present invention incorporates a self-testing feature in its operation.

It happens that an ultrasonic receiver, such as piezo-electric crystal 48, which receives signals through a fluid tube from a diametrically opposed transmitter does not clearly distinguish between a transmitter OFF condition and an air-in-line condition. On the other hand, a distinction between a fluid-in-line condition and an air-in-line condition is relatively easily made. Microprocessor 62 uses these comparative distinctions to advantage. Briefly, since piezo-electric crystal 42 is alternatively excited into ON and OFF conditions according to cycles established by strobe 60, it follows that piezo-electric crystal 48 will receive respective alternating ON and OFF signals if there is fluid in the tube to transmit the signals. The result is that microprocessor 62 receives an alternating output from comparator 62 for the fluid-in-line condition. When an air-in-line condition exists, however, despite the fact crystal 42 is still alternatively excited into ON and OFF conditions, crystal 48 no longer receives the ON condition signal. Instead, crystal 48 receives the OFF condition signal and the air-in-line signal. As stated above, crystal 48 cannot significantly distinguish between these two signals. The result is that microprocessor 62 receives an essentially steady output signal from comparator 68 for the air-in-line condition.

A representation of the signals used by microprocessor 62 for its logic is presented by the graphs shown in FIGS. 6A, 6B, and 6C. These graphs are aligned for respective conditions at any particular time. Specifically, FIG. 6A depicts the output 72 of strobe 60 over a determinable time frame. In FIG. 6A it can be seen that time $t_1$ represents an ON condition for strobe 60 just before it changes to an OFF condition. At time $t_2$ strobe 60 is in the OFF condition and is about to switch back to the ON condition. The condition of strobe 60 at $t_3$ is similar to its condition at $t_1$. Recognize that output 72 could also represent the output of piezo-electric crystal 42. Thus, essentially, output 72 represents the ON and OFF states of the ultrasonic transmitter.

FIG. 6B depicts the output 74 of comparator 68 under a fluid-in-line condition. As discussed above, when there is fluid in the line, the output 74 of comparator 68 should generally track what is input to crystal 42, i.e. the output 72 of strobe 60. As a practical matter, there is some delay between the time when strobe 60 turns OFF and the time at which the output 74 of comparator 68 responds. Thus, there is a lag time 78 which must be compensated for. Consequently, microprocessor 62 is programmed to monitor outputs 72 and 74 at time $t_1$, $t_2$, $t_3$ et. seq in order to avoid a confusing signal such as would be received during time intervals within the time lag 78.

When there is an air-in-line condition, comparator 68 is no longer able to track the output 72 from strobe 60. The result is that for the air-in-line condition, output 76 from comparator 68 is essentially a constant as indicated in FIG. 6C. It should also be recognized that when detector 10 has faulty circuitry, the output 76 of comparator 68 will also be a constant. Thus, with an alternating output 72 from strobe 60, the output 74 of comparator 68 should also alternate substantially as shown in FIG. 6B if there is fluid in tube 14, i.e. a normal operation. On the other hand, according to the logic of microprocessor 62, a constant high or low output 76 from comparator 68 indicates an abnormal condition which must be attended to. Microprocessor 62 can be programmed to provide an alarm signal in abnormal conditions which can be used to cease operation of the device 12.

While the particular ultrasonic air-in-line detector as herein shown and disclosed in detail is fully capable of obtaining the objects and providing the advantages herein before stated, it is to be understood that it is merely illustrative of the presently preferred embodiment of the invention and that no limitations are intended to the details of construction or design herein shown other than as defined in the appended claims.

I claim:

1. An ultrasonic air-in-line detector for use with fluid tubing which comprises:
   a base formed with a cavity;
   a transmitter having a convex lens mounted on said base with said lens protruding into said cavity to contact and indent said tube; and
   a receiver having a convex lens mounted on said base with said lens protruding into said cavity to contact and indent said tube to pinchingly engage said tube between said transmitter and said receiver.

2. A detector as cited in claim 1 further comprising:
   a first pedestal mounted on said base and protruding into said cavity in a direction substantially at right angles to the axis defined between said transmitter and said receiver; and
   a second pedestal hingedly attached to said base for movement into contact with said tube diametrically opposite said first pedestal to pinchingly engage said tube between said first pedestal and said second pedestal.

3. A detector as cited in claim 2 wherein said lenses are made of an epoxy material and said transmitter and said receiver respectively comprise piezo-ceramic crystals to which said lenses are attache by an epoxy adhesive.

4. A detector as cited in claim 3 wherein said second pedestal is mounted on a door and said door is hingedly attached to said base.

5. A detector as cited in claim 4 further comprising:
   means to provide a strobed input to said transmitter which alternates between an ON condition and an OFF condition; and
   electronic means to compare the input to said transmitter with the output of said receiver.

6. A detector as cited in claim 5 further comprising means to create an alarm when said output from said receiver does not track with said input to said transmitter.

7. A detector as cited in claim 6 wherein said lens for said transmitter and said lens for said receiver are spherical convex lenses.

8. A detector as cited in claim 2 wherein said lenses are integrally formed on said base.

9. An ultrasonic device for detecting air in a flexible fluid tube having a predetermined outside diameter which comprises:
   a base;
   a convex-shaped transmitter mounted on said base; and
   a convex-shaped receiver mounted on said base diametrically opposite said transmitter to establish a gap therebetween, said gap being of lesser dimension than the outside diameter of said tube to receive said tube in said gap and pinchingly indent said tube between said transmitter and with said receiver to acoustically couple said tube therebetween.

10. A device as cited in claim 9 further comprising:
    a first pedestal mounted on said base and protruding into said gap in a direction substantially at right angles to the axis defined between said transmitter and said receiver; and
    a second pedestal hingedly attached to said base for movement into contact with said tube diametrically opposite said first pedestal to pinchingly engage said tube between said first pedestal and said second pedestal.

11. A device as cited in claim 10 wherein said lenses are made of an epoxy material and said transmitter and said receiver respectively comprise piezo-ceramic crystals to which said lenses are attached by an epoxy adhesive.

12. A device as cited in claim 11 wherein said second pedestal is mounted on a door and said door is hingedly attached to said base.

13. A device as cited in claim 12 further comprising:
    means to provide a strobed input to said transmitter which alternates between an ON condition and an OFF condition; and
    electronic means to compare the input to said transmitter with the output of said receiver.

14. A device as cited in claim 13 further comprising means to create an alarm when said output from said receiver does not track with said input to said transmitter.

15. A device as cited in claim 14 wherein said lens for said transmitter and said lens for said receiver are spherical convex lenses.

16. A device as cited in claim 10 wherein said lenses are integrally formed on said base.

* * * * *